United States Patent [19]

Kung et al.

[11] Patent Number: 4,670,395

[45] Date of Patent: Jun. 2, 1987

[54] ENANTIOSELECTIVE HYDROLYSIS OF N-ACYLAMINO ACID ESTERS USING A COMBINED ENZYME SYSTEM

[75] Inventors: Wei-Jen Kung, Solon; James D. Burrington, Richmond Hts.; Mark C. Cesa, South Euclid, all of Ohio

[73] Assignee: The Standard Oil Company, Cleveland, Ohio

[21] Appl. No.: 670,255

[22] Filed: Nov. 13, 1984

[51] Int. Cl.$^4$ ............................................ C07P 41/00
[52] U.S. Cl. .................................. 435/280; 435/106; 435/197
[58] Field of Search ............... 435/280, 106, 196, 197

[56] References Cited

U.S. PATENT DOCUMENTS

| | | | |
|---|---|---|---|
| 3,386,888 | 6/1968 | Chibata et al. | 435/280 |
| 3,527,671 | 9/1971 | Zenk et al. | 435/280 |
| 3,813,317 | 3/1972 | Benoiton et al. | 435/280 |
| 3,816,254 | 6/1974 | Chibata et al. | 435/280 |
| 4,108,723 | 8/1978 | Hirohara et al. | 435/280 |

Primary Examiner—Sam Rosen
Assistant Examiner—William J. Herald
Attorney, Agent, or Firm—Charles S. Lynch; John E. Miller; Larry W. Evans

[57] ABSTRACT

Disclosed is combination of an acylase and esterase for selective enzymatic hydrolysis of only the L-isomer of an L and D mixture of αN-acyl-α-amino acid ester whose alpha carbon atom is chiral to yield a mixture containing L-α-amino acid and D-α-N-acyl-α-amino acid ester but essentially no D-α-amino acid.

3 Claims, No Drawings

ENANTIOSELECTIVE HYDROLYSIS OF N-ACYLAMINO ACID ESTERS USING A COMBINED ENZYME SYSTEM

This invention concerns a method of making a mixture containing an L-amino acid essentially free of the enantiomeric D-amino acid from an enantiomeric mixture of L,D-N-acylamino acid ester, which can be optically active (containing an excess of either the L or the D- isomer) or a racemic mixture.

Many naturally occurring α-amino acids can be duplicated synthetically, except that the synthetic products are mixtures of L- and D- isomers. Some of the synthetic methods give N-acyl-α-amino acid esters (or α-amido acid esters) as intermediate products. One example is the Schmidt reaction, described and referenced in the book, *Synthetic Production and Utilization of Amino-Acids*. Kaneko, Izumi, Chibata and Itoh, John Wiley and Sons, New York (1974), on page 14. In the reaction amino acids are obtained from alkyl acetoacetates through the corresponding hydroazoic acid. An N-acyl-amino acid ester is made which is then chemically hydrolyzed to the α-amino acid. Also, in U.S. patent application Ser. No. 552,561, filed Nov. 16, 1983, N-acyl-α-amino acid esters are made by hydrocarboxylation of the appropriate enamide.

It is an object of the invention to provide a process for producing an L-α-amino acid free of enantiomeric D-α-amino acid.

It is another object of the invention to provide a process for selectively enzymatically hydroyzing only the L-isomer of a mixture of the L and D-isomers of an α-N-acylamino acid ester of an α-amino acid having the formula of a naturally occurring α-amino acid whose α carbon atom is chiral.

Other objects, as well as aspects, features and advantages, of the invention will become apparent from a study of the specification, including the specific examples and the claims.

According to the present invention, there is provided a method of making a relatively easily separable mixture containing the L isomer of an α-amino acid having the formula of a naturally occurring α-amino acid whose alpha carbon atom is chiral, said mixture containing said L-isomer being essentially free of the B-isomer, which comprises enzymatically hydrolyzing an L and D mixture of an α-amido acid hydrocarbyl ester derivative of said α-amino acid in the presence of an acylase catalyst and an esterase catalyst to promote hydrolysis of said amido group and the esterified carboxy group of said L-ester, respectively, of said L-isomer only, effecting said hydrolysis, and recovering said L-α-amino acid isomer in admixture with said D-α-amido acid ester derivative containing essentially no enantiomer of said L-α-amiho acid, wherein said hydrocarbyl is a $C_1$ to $C_5$ alkyl group or a benzyl group and the group attached to the carbonyl group of said amido group is a $C_1$ to $C_6$ alkyl group, benzyl, H, phenyl, benzyloxy, trifluoromethyl, trichloromethyl or triphenylmethyl.

In the foregoing process the hydrocarbyl ester of the α-amido acid has the formula

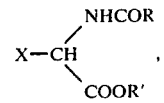

where X is the rest of the naturally occurring α-amino acid of which the α-amido acid ester is a derivative and the carbon linked to X is chiral, R' is the forementioned hydrocarbyl group and R is, of course, the aforementioned group attached to the carbonyl group of said amido group. Of course, X is also substituted when the derivative also has a blocked second acid group or amine group, as in Examples 5 and 10 herein. For instance, in a given instance X can include an amine group not bonded to the chiral carbon, and the amine group can have a -COR group(s) replacing one or both of the H's of such amine group; similarly, the H atom of the additional carboxylic acid group can be replaced by an R' group, where R and R' are as before defined.

There are several advantages to the present method of making an L-amino acid which is free of the D-isomer. First, since the acylase requires the carboxyl group alpha to the amido group in order to catalyze the hydrolysis of the amido group, this automatically prevents hydrolysis thereof at a rate much higher than the ester group and thus prevents a highly basic condition that would cause chemical hydrolysis of both D-and L-isomers. On the other hand, if the rate of hydrolysis promoted by the esterase is much higher than the acylase, the solution will tend to become acidic, but long before the pH is low enough to catalyze chemical hydrolysis, the pH will be too low for the esterase to catalyze the hydrolysis until the pH is automatically raised by the continuing hydrolysis of the amido group catalyzed by the acylase. Ideally, of course, in a given case, it is preferable to adjust the relative amounts of the acylase and the esterase so that the rate of hydrolvsis of the amido group and the ester group are essentially equal. Even in such cases, however, the automatic "buffering" described above prevents any small imbalance over time from creating an acid or a base condition that would promote the non-selective chemical hydrolysis.

As a result of the foregoing, although buffers can be employed in the process of the invention, it is unnecessary to do so and in the preferred practice of the invention the hydrolysis is effected in the absence of buffers. This is certainly an advantage since it eliminates a step of separation of the buffer from the products of the present process.

Of course, a major advantage of the present invention is that the process results in a mixture containing an L-amino acid without D-amino acid. Although part of the N-acyl-α-amino acid ester is also in the product mixture, this derivative is easily separable by known means such as crystallization, solvent extraction, chromatographically, etc., because the presence of the two substituent groups makes the solubilities, crystallization properties, and absorption on solid absorbents so much different that separation is easy.

Another advantage of the present process is that the N-acy-α-amino acid ester, after separation from the amino acid, can be racemized by known methods and recycled to the process, thus ultimately resulting in conversion of essentially all of the starting material derivative to the L-α-amino acid.

In the practice of the process of the invention the esterase can be any suitable esterase. The esterase can be carboxyl esterase, α-chymotrypsin or any other proteases that have esterase activity. The acylase can be aminoacylases from different origins, carboxyl peptidase or other acylases. The starting material L and D-α-amido acid ester is usually dissolved in a suitable aqueous solvent, either water or water containing a polar organic solvent including (1) 0–50, usually 0–40 volume percent lower alcohol, especially methanol or ethanol (or both), or (2) 0–40, usually 0–30, volume percent acetone or 0–40, usually 0–30, volume percent acetonitrile. Preferably the lower limit of all of the above systems is for at least 10 volume percent of the organic solvent to be present in the aqueous solution. Obviously, also, a mixture of any of the polar solvents can be used in the aqueous system.

The starting material mixture of D and L-N-acylamino acid ester is usually at a concentration of 0.05 to 0.5M in the solvent, although higher or lower concentrations can be used.

When operating the process as a batch reaction, the enzymes are each usually present in the reaction mixture in the concentration of 100–500 units per liter of reaction mixture, although higher and lower amounts can be used. They are usually immobilized on a support by methods well known in the art, but need not be, except that when an esterase is used that will react with the acylase used, the acylase or the esterase is immobilized on a support to prevent this. Also, it is usually advantageous to immobilize both enzymes on a support, either the same support or a different support for each enzyme. This has the advantage that the liquid reaction product is easily removed from the enzymes by simple filtration, settling, centrifugation, or the like. The supported enzymes in the case of a batch reaction can be washed and used again. When carrying out the hydrolysis by passing the α-amido acid ester solution continuously over a packed bed containing the immobilized enzymes, washing of the catalyst bed is not even needed.

When carrying out the reaction as a batch reaction usual time of reaction is 3–50 or 100 hours, although higher or lower reaction times can be used and reaction time is by no means the essence of the invention, nor are any other details of the reaction conditions. When operating continuously in a packed column suitable contact times are from 10 minutes to 4 hours, although, again, lower or higher contact times can be used.

EXAMPLE 1

The support for the acylase enzyme used in this example was cross-linked dextran substituted with diethylamino ethyl groups attached through an oxygen of an OH group. It was obtained in bead form from Sigma chemical Co., St. Louis, Mo., under the name DEAE Sephadex resin, grade A25. Five grams of this resin was suspended in 50 ml. of water. With stirring, 250 ml. of 0.1N NaOH was added to the suspension and stirring was continued for 3 hours. The suspension was filtered, the filter cake washed thoroughly with deionized water. The filter cake was then suspended with stirring for 3 hours in 250 ml. of an 0.1M potassium phosphate buffer (pH 7.0) and the left standing overnight.

200 mg. of aminoacylase (E.C. 3.5.1.14) powder from Aspergillus species from Sigma chemical Co., St. Louis, Mo. containing about 40 percent acylase protein was dissolved in 83 ml. of distilled water and then filtered. The suspension of the treated dextran resin described above was filtered and the filter cake dispersed in the filtrate containing the aminoacylase. The mixture was stirred for 3 hours at room temperature and filtered. The filter cake was dispersed in 250 ml. of deionized water, stirred 1 hour, then filtered. The filter cake was dispersed in 250 ml. of 0.2M sodium acetate and the suspension stirred for 1 hour, filtered and the filter cake washed several times with deionized water. The immobilized acylase (50 units) of about 5 grams, suspended in about 15 ml. of water, 1 ml. of 10 mM $CoCl_2$, and 50 units of α-chymotrypsin immobilized on about 100 mg. of carboxymethylcellulose (CMC) were added at room temperature with stirring to a solution of 1.32 grams of N-acetyl-D,L-phenylalanine methyl ester in 20 ml. of a 33 volume percent methanol/67 percent water solution.

The immobilized α-chymotrypsin on CMC esterase was obtained from Sigma Chemical Co., supra.

The pH of the foregoing reaction mixture was 7.5; no pH adjustment was needed. After 36 hours of the hydrolysis reaction at room temperature, the reaction mixture was filtered to remove the solid immobilized enzymes from the suspension, the filter cake was washed two times with 20 ml of 33 percent methanol, 67 percent water solution, the washings and the original filtrate were combined, concentrated to about 15 ml., cooled to 4° C. and held at that temperature overnight. Crystalline precipitate formed and was filtered out. These crystals were identified as the N-acetyl-D-phenylalanine methyl ester using a chiral gas chromatograph column (Chiralsil-Val III from Alltech Associates, Inc., Deerfiled, Ill.) operated at 170° C. isothermal. The crystals were more than 99 percent pure (optical purity). The filtrate was washed three times with 10 ml of ethyl ether, the ether layer separated from the water-methanol layer and evaporated to give crystals of N-acetylphenylalanine methyl ester (25% L, 75% D using thin layer chromatoqraphy and optical rotation measurements). No D-phenylalanine was detected in this portion of the product.

The aqueous layer was evaporated almost to dryness to give 430 mg. of product about an 87% yield. Thin layer chromatography and optical purity measurements established that over 97 percent of this precipitzte was L-phenylalanine with the balance being N-acetylphenylalanine methyl ester. No detectable D-phenylalanine was present in this fraction of the product.

No D-phenylalanine was detectable in any fraction of the product of the reaction. Thus the hydrolysis reaction resulted in a mixture containing L-phenylalanine and D-acetylphenylalanine methyl ester but no D-phenylalanine.

EXAMPLES 2-38

In a manner similar to Example 1, each of the racemic α-N-acyl-α-amino acid esters (α-amido acid esters) shown in the first column of Table I are subjected to the enzymatic hydrolysis to selectively convert only L-α-amido acid esters by hydrolyzing α-amido groups thereof and hydrocarbyl carboxy groups thereof, thus producing a mixture containing the L-isomer of the corresponding α-amino acid and unchanged D-α-N-acyl amino acid ester and no D-α-amino acid. In these examples the acylase used is the same as was used in Example 1, immobilized on the same support. The particular esterase employed in each example is indicated in the second column of Table 1.

In these examples 6 millimoles of the α-amido acid ester is dispersed in 20 ml. of a 30 percent methanol-70 percent water solution by volume. In Examples 3, 4, 11, 22 and 34 the pH is adjusted to about 7.8 by adding dilute acetic acid thereto. Then in all examples 2 ml. of 10 mM CoCl₂ and 10 grams of cross-linked dextran substituted with diethylamino ethyl groups on which are immobilized 400 mg. of aminoacylase (E.C. 3.5.1.14), or 100 units, plus 100 units of the esterase listed in the second column of Table 1 are added. The acylase used in these examples is the same as used in Example 1. Then the reaction mixture is stirred, heated to, and held at, a temperature of 50° C. until thin layer chromatography shows substantial conversion of the starting material is effected. Thereafter the reaction mixture is filtered to remove the supported enzyme. giving a filtrate containing the L-α-amino acid resulting from the hydrolysis in admixture with the D-N-acyl-α-amino acid ester starting mateial, which mixture is free of the D-α-amino acid enantiomer.

Since in Examples 5 and 10 the starting materials have second ester groups, the α-amino acid products are, respectively, $$H_3COOCCH_2CHCOOH \text{ and } H_3COOCCH_2CH_2CHCOOH$$
$$\quad\quad\quad\quad |\quad\quad\quad\quad\quad\quad\quad\quad\quad\quad\quad |$$
$$\quad\quad\quad\quad NH_2\quad\quad\quad\quad\quad\quad\quad\quad\quad NH_2$$

TABLE I

| Example No. | Reactant (racemic mixture) | Identity Of Esterase |
|---|---|---|
| 2 | N—acetylalanine ethyl ester | α-Chymotrypsin (E.C. 3.4.21.) |
| 3 | α-N—formylarginine propyl ester | Trypsin (E.C. 3.4.21.4) |
| 4 | α-N—acetylasparagine methyl ester | Chymotrypsin C (E.C. 3.4.21.2) |
| 5 | N—acetylaspartic acid dimethyl ester | Staphyloccocal serine proteinase (E.C. 3.4.21.19) |
| 6 | N—propionylcysteine methyl ester | carboxyl esterase (E.C. 3.1.1.1) |
| 7 | N,N'—diacetylcystine dimethyl ester | carboxyl esterase (E.C. 3.1.1.1) |
| 8 | N—formyl-3,5-Dibromotyrosine methyl ester | α-Chymotrypsin (E.C. 3.4.21.1) |
| 9 | N—acetyl-3,5-Diiodotyrosine ethyl ester | α-Chrymotrypsin (E.C. 3.4.21.1) |
| 10 | N—isobutyrylglutamic acid dimethyl ester | Staphylococcal serine proteinase (E.C. 3.4.21.19) |
| 11 | α-N—acetylglutamine methyl ester | Chymotrypsin C (E.C. 3.4.21.2) |
| 12 | α-N—formylhistidine ethyl ester | carboxyl esterase (E.C. 3.1.1.1) |
| 13 | α-N—acetylhydroxylysine methyl ester | Trypsin (E.C. 3.4.21.4) |
| 14 | N—propionylhydroxyproline methyl ester | carboxyl esterase (E.C. 3.1.1.1) |
| 15 | N—acetyl-β-Cyanoalanine methyl ester | carboxyl esterase (E.C. 3.1.1.1) |
| 16 | N—acetyl-3,5-Diiodotyrosine ethyl ester | α-chymotrypsin (E.C. 3.4.21.1) |
| 17 | α-N—acetyl-3-methylhistidine methyl ester | carboxyl esterase (E.C. 3.1.1.1) |
| 18 | α-N—acetylcanavanine methyl ester | carboxyl esterase (E.C. 3.1.1.1) |
| 19 | α-N—formylazaserine methyl ester | carboxyl esterase (E.C. 3.1.1.1) |
| 20 | N—acetylisoleucine methyl ester | subtilisin (E.C. 3.4.21.14) |
| 21 | N—acetylleucine methyl ester | subtilisin (E.C. 3.4.21.14) |
| 22 | α-N—formyllysine ethyl ester | trypsin (E.C. 3.4.21.4) |
| 23 | N—acetylmethionine methyl ester | αchymotrypsin (E.C. 3.4.21.1) |
| 24 | N—acetylproline ethyl ester | subtilisin (E.C. 3.4.21.14) |
| 25 | N—acetylserine methyl ester | carboxyl esterase (E.C. 3.1.1.1) |
| 26 | N—propionylthreonine methyl ester | carboxyl esterase (E.C. 3.1.1.1) |
| 27 | N—acetylthyroxine ethyl ester | carboxyl esterase (E.C. 3.1.1.1) |
| 28 | α-N—formyltryptophane butyl ester | α-chymotrypsin (E.C. 3.4.21.1) |
| 29 | N—acetyltryosine methyl ester | α-chymotrypsin (E.C. 3.4.21.1) |
| 30 | N—isobutyrylvaline methyl ester | subtilisin (E.C. 3.4.21.1) |
| 31 | N—acetyl-4-hydroxyproline methyl ester | carboxyl esterase (E.C. 3.1.1.1) |
| 32 | N—acetyl-5-hydroxylysine methyl ester | carboxyl esterase (E.C. 3.1.1.1) |
| 33 | N—acetyl-1-aminocyclopropane-1-carboxylic acid ethyl ester | carboxyl esterase (E.C. 3.1.1.1) |
| 34 | N—acetylornithine methyl ester | trypsin (E.C. 3.4.21.4) |
| 35 | N—formylthyroxine methyl ester | carboxyl esterase (E.C. 3.1.1.1) |
| 36 | N—acetyl-3,5,3'-triiodothyroxine methyl ester | carboxyl esterase (E.C. 3.1.1.1) |
| 37 | N—formylcitrulline ethyl ester | carboxyl esterase (E.C. 3.1.1.1) |
| 38 | Acetyl-3,4-dihydroxyphenylalanine methyl ester | chymotrypsin (E.C. 3.4.21.1) |

We claim:

1. A method which comprises enzymatically hydrolyzing selectively the L-isomer of an L and D mixture of an α-amido acid hydrocarbyl ester derivative of an α-amino acid having the formula of a naturally occurring α-amino acid whose alpha carbon atom is chiral, in the presence of an acylase catalyst and an esterase catalyst to promote hydrolysis, respectively, of said alpha amido group and the esterified carboxy group of said L-ester only, effecting said hydrolysis by said acylase catalyst and by said esterase catalyst, and recovering the resulting L-α-amino acid in admixture with said D-α-amido acid hydrocarbyl ester derivative and containing essentially no D-α-amino acid enantiomer of said L-α-amino acid, wherein said hydrocarbyl is a C₁ to C₆ alkyl group or a benzyl group and the group attached to the carbonyl carbon of said amido group is a C₁ to C₆ alkyl group, benzyl, H, phenyl, benzyloxy, trifluoromethyl, trichloromethyl or triphenylmethyl.

2. A method of claim 1 wherein both enzymes are immobilized on a solid support.

3. A method of claim 1 wherein at least one of the enzymes is immobilized on a solid support.

* * * * *